US008377915B2

(12) United States Patent
Gorelick-Feldman et al.

(10) Patent No.: US 8,377,915 B2
(45) Date of Patent: Feb. 19, 2013

(54) METHODS FOR TREATING OR PREVENTING DISORDERS USING ECDYSTEROID COMPOSITIONS

(75) Inventors: Jonathan Gorelick-Feldman, Highland Park, NJ (US); Ilya Raskin, Manalapan, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1038 days.

(21) Appl. No.: 11/799,598

(22) Filed: May 2, 2007

(65) Prior Publication Data

US 2007/0265235 A1 Nov. 15, 2007

Related U.S. Application Data

(60) Provisional application No. 60/800,844, filed on May 9, 2006.

(51) Int. Cl.
*A61K 31/56* (2006.01)
(52) U.S. Cl. ........................ 514/181; 514/182
(58) Field of Classification Search ................. 514/181, 514/182
See application file for complete search history.

(56) References Cited

U.S. PATENT DOCUMENTS

| | | | | |
|---|---|---|---|---|
| 5,198,225 A * | 3/1993 | Meybeck et al. | | 424/450 |
| 2005/0086713 A1 | 4/2005 | Karunanandaa et al. | | |
| 2005/0191385 A1 | 9/2005 | Amato | | |

FOREIGN PATENT DOCUMENTS

CN 1 279 951 A 1/2001

OTHER PUBLICATIONS

Tsitsimpikou et al., Rapid Communications in Mass Spectrometry, 2001;15:1796-1801.*
Cohen-Solal et al., European Heart Journal, 1999:20:931-945.*
Bruno, "20-hydroxyecdysone: The Pro-anabolic Steroid" in Smart Supplementation, 2001, published by Huntington College of Health Sciences.*
H.B. Segard et al., "Autocrine Growth Hormone Production Prevents Apoptosis and Inhibits Differentiation in C2C12 Myoblasts", Cellular Signalling 15 (2003), pp. 612-623, Elsevier Science, Inc.
A. A. Butler et al., "Control of Growth by the Somatropic Axis: Growth Hormone and the Insulin-Like Growth Factors have Related and Independent Roles", Annu. Rev of Physiology 2001, v. 63, pp. 141-164, Downloaded from arjournals.annualreviews.org, Rutgers University Libraries Aug. 10, 2007.
R.F. Wolf et al., "Growth Hormone and Insulin Combine to Improve Whole-Body and Skeletal Muscle Protein Kinetics", Surgery, (Aug. 1992), v. 112, pp. 284-292, from the Surgical Metabolism Laboratory, Dept. of Surgery, Memorial Sloan-Kettering Cancer Center, New York, New York.
J. L. Kostyo, "Rapid Effects of Growth Hormone on Amino Acid Transport and Protein Synthesis", Annals New York Academy of Sciences, (1968), v. 148, pp. 389-407.
Courtheyn et al., Recent developments in the use and abuse of growth promoters. *Anal. Chimica Acta*, 473(1-2): 71-82 (2002).
Gyula et al., Doping agent and their analytical control. *Acta Pharma. Hungaria*, 72(4): 231-44 (2002).
Jin et al., Effects of ecdysterone on collateral formation and expression of VEGF in rat with acute myocardial infarction. *Database CA—Chemical Abstracts Services*, 16(4): 459-61 (2000).
Wu et al., Beneficial effect of ecdysterone on rat myocardial infarction induced by coronary occlusion. *Database CA—Chemical Abstracts Services*, 32(8): 721-3 (2001).
Wu et al., Use of ecdysterone in preparing medicine for angiocardiopathy. *Database EPODOC—European Patent Office*, 2001.
Grebenok et al., Occurrence and levels of ecdysteroids in spinach. *Lipids*, 26(8): 666-8 (1991).
Supplementary European Search Report and Written Opinion, EP 07 79 4524, European Patent Office, dated Aug. 24, 2009.
International Search Report, PCT/US2007/10772, United States Patent and Trademark Office, dated Oct. 23, 2007.
Written Opinion of the International Searching Authority, PCT/US2007/10772, United States Patent and Trademark Office, dated Oct. 23, 2007.
International Preliminary Report on Patentability, PCT/US2007/10772, dated Nov. 11, 2008.

* cited by examiner

*Primary Examiner* — San-Ming Hui
(74) *Attorney, Agent, or Firm* — Marshall, Gerstein & Borun LLP

(57) ABSTRACT

This invention relates to methods and compositions which are useful in the modulation of endogenous growth hormone levels in a mammal. Also included are methods of treating a mammal which include the administration of said compositions.

9 Claims, No Drawings

METHODS FOR TREATING OR PREVENTING DISORDERS USING ECDYSTEROID COMPOSITIONS

CROSS REFERENCE TO RELATED APPLICATION

This application claims the benefit of U.S. Provisional Patent Application No. 60/800,844, filed May 8, 2006, the entirety of which is hereby incorporated by reference into this application.

BACKGROUND OF THE INVENTION

1. Field of the Invention

The present invention relates to compositions comprising ecdysteroid and methods of using the compositions to treat or prevent a physiological condition related to growth hormone.

2. Description of Related Art

Growth hormone (GH) plays a key role in growth and metabolism. Growth hormone, also known as somatotropin, exerts some of its effects directly on the tissues and other effects indirectly by inducing the synthesis of growth factors. The most important of these growth factors are the insulin-like growth factors (Butler and LeRoith, *Annu. Rev. Physiol.* 63:141-64, 2001).

GH has wide-ranging developmental effects on the organism. GH administration to animals induces protein synthesis in muscle and positive nitrogen balance (Kostyo, *Ann. NY Acad. Sci.* 148:389-407, 1968). GH administration also enhances amino acid uptake into skeletal muscle, suggesting that this tissue is a primary target (Segard et al., *Cellular Signaling* 15:615-623, 2003).

In cases where increased levels of growth hormone are desired, treatments have included providing exogenous growth hormone, and administering GHRH or other peptidyl compounds which stimulate growth hormone production or release. In such cases, the peptidyl nature of the compound has necessitated that it be administered by injection. There is a need for a treatment that is simpler to administer and less painful.

Various health issues and disease states have been traced to deficiencies in maintaining normal growth hormone levels. For example, certain medical conditions associated with aging are due to age-related reduction in GH levels. Administration of growth hormone is used to treat conditions related to growth hormone deficiency. Clinical studies indicate that growth hormone supplementation may be useful in combating the maladies of aging in humans. Growth hormone is also used to treat human dwarfism.

Treatment of GH-deficient individuals with human GH has been shown to increase muscle size (Wolf et al., *Surgery* 112:284-91, 1992). GH therapy increases whole body protein synthesis, enhances nitrogen retention, and consequently increases the lean muscle mass (Wolf et al., 1992, supra).

SUMMARY OF THE INVENTION

The present invention relates to a method and composition for increasing the production of growth hormone in vertebrates and particularly in mammals.

One embodiment of the present invention relates to a method for increasing the level of growth hormone in mammalian tissue comprising contacting the tissue with a composition comprising an ecdysteroid at a concentration that is effective to increase growth hormone transcription. Although the primary site of GH production is the pituitary gland, local production in muscle and other tissues may also be physiologically important. For example, autocrine GH production is known to enhance the proliferation of muscle cells (Segard et al., 2003, supra).

In another embodiment, the present invention relates to a method for the treatment or prevention of a physiological disorder by increasing the level of growth hormone in mammalian tissue comprising administering to a mammal in need of treatment a composition comprising an ecdysteroid wherein the concentration of ecdysteroid is sufficient to increase growth hormone transcription in tissue.

The present invention further relates to a method for the treatment or prevention of a physiological disorder that is related to a growth hormone deficiency. The method comprises administering to a mammal in need of said treatment a composition comprising an ecdysteroid wherein the concentration of ecdysteroid is sufficient to increase growth hormone transcription in tissue.

It is contemplated that for the methods described herein the ecdysteroid is a phytoecdysteroid, synthesized by plants or an ecdysteroid synthesized by members of the phylum arthropoda or a synthetic version thereof. Preferably, the ecdysteroid is 20-hydroxyecdysone (20HE). An ecdysteroid composition can be a plant extract. For example, the ecdysteroid composition can be an extract of spinach.

It is further contemplated that for the methods of treatment the administration of the composition includes all modes known in the art for delivering therapeutic compositions to a mammal. Preferably, the composition can be orally administered.

Pharmaceutical compositions comprising ecdysteroid at a concentration suitable for increasing transcription of growth hormone in vertebrate tissue and one or more pharmaceutically acceptable formulation agents are also encompassed by this invention. It is contemplated that the ecdysteroid is a phytoecdysteroid, synthesized by plants or an ecdysteroid synthesized by members of the phylum arthropoda or a chemically synthesized molecule. Preferably, the ecdysteroid is 20-hydroxyecdysone (20HE).

The present invention further relates to pharmaceutical formulations containing compounds comprising ecdysteroid, alone or in combination with other compounds that increase the endogenous levels of growth hormone in a mammal. The use of these compounds and/or formulations to increase endogenous levels of growth hormone in a mammal is also contemplated. Further contemplated is the use of these compounds and/or formulations to treat or prevent muscle degradation, treat or prevent muscle atrophy, treat cachexia, increase muscle mass or treat, inhibit or prevent symptoms and/or disease of congestive heart failure or myocardial infarction.

These and other embodiments of the subject invention will be apparent to one of skill in the art in view of the disclosure herein.

DETAILED DESCRIPTION

It has been discovered that ketosteroid compounds known as ecdysteroids, which include both phytoecdysteroids from plants and ecdysteroids produced by members of the phylum arthropoda, have the effect of causing an increase in the protein somatotropin, also known as growth hormone (GH). The present invention relates to a method for increasing the production of growth hormone in vertebrate tissue by administering a composition which contains ecdysteroid at a concentration sufficient to increase growth hormone transcription.

A first embodiment of the present invention is a method for increasing the level of growth hormone in mammalian tissue by contacting the tissue with a composition comprising an ecdysteroid at a concentration that is effective to increase growth hormone transcription. Both phytoecdysteroids and ecdysteroids produced by the phylum arthropoda are contemplated. Preferably, the ecdysteroid is 20-hydroxyecdysone. The effective human dose is between about 0.01 mg/kg of patient weight per day to 5 mg/kg of patient weight per day.

In another embodiment, the present invention relates to a method for the treatment or prevention of a physiological disorder by increasing the level of growth hormone in mammalian tissue comprising administering to a mammal in need of treatment a composition comprising an ecdysteroid wherein the concentration of ecdysteroid is sufficient to increase growth hormone transcription in tissue. Example physiological disorders include muscle degeneration, muscle atrophy, cachexia, symptoms and/or disease of congestive heart failure or myocardial infarction. The mammal can be human.

Another embodiment of the invention is a method for the treatment or prevention of muscle degradation comprising administering a composition comprising an ecdysteroid at a sufficient concentration to increase growth hormone transcription in muscle.

Another embodiment of the invention is a method of treatment for a growth hormone deficiency comprising administering a composition comprising an ecdysteroid wherein the concentration of ecdysteroid is sufficient to increase growth hormone transcription in tissue.

Another embodiment of the invention is a method for the treatment or prevention of a physiological disorder that is related to a growth hormone deficiency. The method comprises administering to a mammal in need of the treatment an ecdysteroid-containing composition wherein the concentration of ecdysteroid is sufficient to increase growth hormone transcription in tissue. Specific conditions and/or disease states involving growth hormone deficiency that may be treated with the methods and compounds of the invention include, but are not limited to, dwarfism and age-related growth hormone deficiency disorders.

The ecdysteroid composition can be an extract from a plant such as spinach. The term "extract" as used herein means a substance or composition obtained from a plant or plant part source, regardless of whether the substance or composition is found external to the plant (i.e., an exudate), is found within the plant or plant part but external to the cells thereof, or is found within the cells of the plant. Chemical and/or physical action, as would be understood in the art, may be required to obtain the substance or composition from the plant or plant part. For the methods of treatment of this invention, a typical treatment course may comprise administration of multiple doses on a daily basis of a composition comprising an amount of an ecdysteroid effective to increase growth hormone production in an individual. Such a treatment course may be continued for significant periods of time, for example, three doses per day over three months or even indefinitely. In one embodiment, a presently preferred dosing schedule is one dose per day. The treatment may be continued on an as-needed basis.

The foregoing are only exemplary treatment schedules, and other schedules are contemplated. In each case, the suitability of such schedules and the aforementioned modes of administration are determined by those of skill in the art, using routine procedures. For example, those of skill in the art will be able to take the information disclosed in this specification and optimize treatment regimes for human subjects based on clinical trials performed in accordance with the specification.

Various modes of administration are contemplated for use in delivering the composition containing ecdysteroid. These include all modes known in the art for delivering therapeutic compositions to a mammal such as a human patient. Modes of administration include e.g., oral, nasal, parenteral (e.g., intravenous, intramuscular and subcutaneous), transdermal and topical. The active ecdysteroid can be added to a pharmaceutically acceptable formulation, nutraceutical, and/or food in any suitable amount. In one embodiment, the pharmaceutically acceptable formulation, nutraceutical, and/or functional food comprises the ecdysteroid in an amount of at least 0.1% by weight to about 95% percent by weight.

For the methods of treatment of this invention, a typical treatment course may comprise administration of multiple doses on a daily basis of a composition comprising one or more compounds of the present invention in an amount effective to treat a disorder such as treating or ameliorating symptoms of muscle degeneration, muscle atrophy, cachexia, congestive heart failure or myocardial infarction. Such a treatment course may be continued for significant periods of time, for example, three doses per day over three months or even indefinitely. In one embodiment, a presently preferred dosing schedule is one dose per day. The treatment may be continued on an as-needed basis. The particular dosage of a compound required to treat, inhibit, or prevent the symptoms and/or disease of congestive heart failure in a mammal, including humans, according to this invention will depend upon the particular disease, symptoms, and severity. Dosage, routes of administration, and frequency of dosing is best decided by the attending physician. Generally, accepted and effective doses will be from 1 mg/day to 200 mg/day, and more typically from 5 mg/day to 80 mg/day. Such dosages will be administered to a patient in need of treatment from one to three times each day or as often as needed for efficacy.

In one embodiment, the pharmaceutical compositions containing ecdysteroid may be in any form suitable for oral use, such as e.g., tablets, troches, lozenges, aqueous or oily suspensions, dispersible powders or granules, emulsions, hard or soft capsules, or syrups or elixirs. Compositions intended for oral use can be prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations.

According to the invention, tablets contain the active ingredient(s) in admixture with non-toxic pharmaceutically acceptable excipients, such as inert diluents, granulating, disintegrating and lubricating agents, which are suitable for the manufacture of tablets. Binders may be used to hold the composition comprising the ecdysteroid product together to form a hard tablet. Exemplary binders include materials from natural products such as acacia, tragacanth, starch and gelatin. Other suitable binders include methyl cellulose (MC), ethyl cellulose (EC), and carboxymethyl cellulose (CMC). The tablets may be uncoated or they may be coated by known techniques to delay disintegration and absorption in the gastrointestinal tract and thereby provide a sustained action over a longer period. The formulations can also be so constituted that they release the active ingredient only or preferably in a particular part of the intestinal tract, possibly over a period of time. Such formulations would involve coatings, envelopes, or protective matrices which may be made from polymeric substances or waxes.

Formulations for oral use may also be presented as hard gelatin capsules wherein the active ingredient is mixed with an inert solid diluent, or as soft gelatin capsules wherein the active ingredient is mixed with water or an oil medium.

Aqueous suspensions contain the active material in admixture with excipients suitable for the manufacture of aqueous suspensions, such as e.g., suspending agents, dispersing or wetting agents, preservatives, coloring agents, flavoring agents, and sweetening agents. Dispersible powders and granules suitable for preparation of an aqueous suspension by the addition of water provide the active ingredient(s) in admixture with a dispersing or wetting agent, suspending agent and one or more preservatives. Additional excipients, for example sweetening, flavoring and coloring agents, may also be present.

The ecdysteroid-containing compositions also may be formulated as a food or beverage additive as defined by the U.S. Food and Drug Administration. In one embodiment, the ecdysteroid-containing compositions include at least one formulation agent selected from the group consisting of diluents, fillers, salts, binders and biologically acceptable carriers.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The compositions, and thus the methods, of the invention can be used alone or in conjunction with other therapies including, for example, administration of other therapeutic agents including other growth hormone-inducing compounds.

The methods in accordance with the invention contemplate administration of the composition comprising an ecdysteroid whether or not symptoms are manifest, i.e., prophylactic administration is contemplated. The particular dosage of a compound required to treat, inhibit, or prevent the symptoms and/or disease due to growth hormone deficiency in a mammal, including humans, according to this invention will depend upon the particular disease, symptoms, and severity. Dosage, routes of administration, and frequency of dosing are best decided by the attending physician. Such dosages are to be administered to a patient in need of treatment from one to three times each day or as often as needed for efficacy.

It will be appreciated that the treatment methods of the invention are useful in the fields of human medicine and veterinary medicine. Thus, the subject or individual to be treated may be a mammal, preferably human, or other animals. For veterinary purposes, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

It is contemplated that another application of the present invention is the administration of a composition comprising an ecdysteroid to an animal on a schedule that results in increasing lean muscle mass. It is contemplated that this application of the method described herein will result in production of leaner meat products or in the production of larger and/or stronger animals.

The following examples are provided to describe the invention in greater detail, and are intended to illustrate, not to limit, the appended claims. Example 1 provides in vitro evidence that ecdysteroid compositions affect the transcription of various mRNAs in a manner that deviates from the effect of an anabolic steroid. Example 2 provides in vitro evidence that ecdysteroid compositions affect transcription of mRNA for growth hormone.

Example 1

Microarray Comparison of Transcription in Cells Contacted with 20 HE or Methandrostenolone A transcriptome approach utilizing cDNA microarray was implemented to observe the unique effects of ecdysteroids. Microarray analyses was developed and implemented to discern the transcriptional differences between ecdysteroids and anabolic steroids.

Cell Culture

Two cell lines were tested in parallel.

A mouse skeletal muscle cell line, C2C12, (ATCC) was seeded between 4 and 20 passages at a density of $10^5$ cells/$cm^2$ onto 10 cm tissue culture plates. The cells were grown in DMEM supplemented with 10% Fetal Bovine Serum, 10 mM HEPES, 6 mM Glutamine, 1 mM pyruvate, 100 U/ml penicillin, and 100 ug/ml streptomycin.

A mouse Leydig cell line, TM3, (ATCC) was seeded between 5 and 20 passages at a density of $10^5$ cells/$cm^2$ onto 10 cm tissue culture plates. The cells were grown in F12/DME media supplemented with 5% horse serum, 2.5% fetal bovine serum, 100 U/ml penicillin, and 100 µg/ml streptomycin.

Cells were grown for 48 hours in 5% $CO_2$ at 37° C. until they approached 80% confluency. Cells were washed with serum free DMEM and treated with either 1 µM 20-hydroxysterone (20HE), or methandrostenolone (synthetic anabolic steroid). Both compounds were dissolved in 70% ethanol and added to serum free media. Cells were incubated after treatment for 18 hours before RNA extraction.

RNA was extracted and purified from C2C12 myoblasts and TM3 Leydig tumor line cells using an RNeasy kit according to the manufacturer's instructions (Qiagen). RNA concentration and purity were assessed using a spectrophotometer. All RNA samples used had 260/280 ratios greater than 1.9.

A collection of 21,900 oligonucleotides was purchased from Compugen, Inc. Microarrays were printed on poly-L-lysine-coated glass slides using an OmniGrid microarrayer (GeneMachines, San Carlos, Calif.) and quill-type printing pins (Telichem, Sunnyvale, Calif.) following standard procedures. Fluorescent probes were prepared from 5 µg of total cellular RNA using the Genisphere 3DNA dendrimer system (Genisphere, Inc., Montvale, N.J.). Two separate microarrays, one for each cell line, were run. The ecdysone treated RNA sample was labeled with Cy3 and the methandrostenelone treated RNA sample was labeled with Cy5 in a parallel reaction, mixed, and hybridized to the chips. Automated microarray hybridization and washing were performed using a Ventana Discovery System. The sequence-tagged target was hybridized for 12 hours at 58° C., and microarrays were washed twice in 2 µM SSC for 10 minutes at 55° C. and once in 0.1 µM SSC for 2 minutes at 42° C. Florescent dendrimer was then applied and incubated at 55° C. for 2 hours. The microarrays were then washed with 2 µM SSC and spin-dried, followed by scanning on an Axon GenePix 4000B. Image files were processed using Axon GenePix 4.0 software, resulting in text files containing median fluorescence intensities as well as median local backgrounds. Normalized data were imported along with spot flag information into GeneSpring where the ratios were calculated.

Results

Computational analysis of the two treatments revealed genes with at least 2-fold difference in expression, as shown in Tables 1 and 2. In C2C12, 278 genes were up-regulated more than 2-fold by 20HE as compared to methandrostenolone and 479 genes were down-regulated more than two fold. In TM3, 287 genes were up-regulated more than 2 fold by 20HE as compared to methandrostenolone and 341 genes were down-regulated more than 2 fold.

Growth hormone was identified as a potential gene of interest. In C2C12, 20-HE increased growth hormone expression 3.2 times more than methandrostenolone. In TM3, 20-HE increased growth hormone expression 7.0 times more than methandrostenolone.

TABLE 1

TM3 Differential Gene Expression

| LL | Title | Gene Description | Ontology | 20E/D Expr |
|---|---|---|---|---|
| 20297 | Chemokine (C—C motif) ligand 20 | small inducible cytokine subfamily A20 (Scya20) | immune response | 11.89 |
| 14599 | Growth hormone | hormone activity | polyubiquitylation | 7.006 |
| 68349 | Ndufs3 | NADH dehydrogenase (ubiquinone) Fe—S protein 3 | mitochondrial electron transport | 4.741 |
| 20905 | Steroid sulfatase | steroid sulfatase (Sts) | steroid metabolism | 4.611 |
| 27047 | Osteomodulin | osteomodulin (Omd) | skeletal development | 0.010 |
| 18227 | Nuclear receptor subfamily 4, group A, member 2 | steroid hormone receptor activity; ligand-dependent nuclear receptor activity; DNA binding; transcription factor activity | transcription regulation | 0.010 |
| 23920 | Insulin receptor-related receptor | transmembrane receptor protein tyrosine kinase signaling pathway; transport; protein amino acid phosphorylation | cell-cell signaling | 0.022 |
| 20846 | Signal transducer and activator of transcription 1 | signal transduction | transcription regulation | 0.052 |
| 16334 | Insulin II | hormone activity | glucose metabolism | 0.262 |

TABLE 2

C2C12 Differential Gene Expression

| LL | Title | Gene Description | Ontology | 20E/D Expr |
|---|---|---|---|---|
| 11747 | Annexin A5 | blood coagulation | immune response | 11.90 |
| 14964 | Histocompatibility 2, D region locus 1 | sperm specific antigen 1 (Ssfa1) | fertilization | 6.771 |
| 17149 | mago-nashi homolog, proliferation-associated | sex determination; female gamete generation | developmental processes | 3.708 |
| 14599 | Growth hormone | hormone activity | polyubiquitylation | 3.163 |
| 12424 | Cholecystokinin | hormone activity | signal transduction | 0.010 |
| 13163 | Fas death domain-associated protein | protein binding; transcriptional repressor activity | induction of apoptosis via death domain receptors | 0.010 |
| 14166 | Fibroblast growth factor 11 | signal transduction | cell cycle control | 0.010 |
| 15277 | Hexokinase 2 | hexokinase activity; ATP binding; catalytic activity; transferase activity | glycolysis | 0.010 |
| 23920 | Insulin receptor-related receptor | transmembrane receptor protein tyrosine kinase signaling pathway; transport; protein amino acid phosphorylation | cell-cell signaling | 0.020 |

Example 2

Quantitative Real Time RT-PCR of Differential Gene Expression in Murine Cell Lines Treated with 20-Hydroxyecdysone or Methandrostenolone 20-HE increased expression of GH in both the C2C12 muscle cell line and the TM3 Leydig tumor line. This was shown through cDNA microarray analysis and confirmed using Real-Time RT-PCR.

Selected microarray results were verified by comparison with mRNA levels obtained by Real Time reverse transcription PCR (qRT-PCR). Selected gene-specific primer pairs were designed for the mouse growth hormone and glyceraldehyde-3-phosphate dehydrogenase genes using the Primer Express software, as shown in Table 3. Total RNA was isolated, DNase I-treated, and first-strand cDNA was synthesized using Stratascript reverse transcriptase with random primers. The PCR reactions were carried out using 500 ng of cDNA, 150 nM of each primer, and SYBR Green master mix in 25 µL reactions. Levels of quantitative reverse transcription product were measured using SYBR Green fluorescence collected during real-time PCR on a Stratagene MXP3000 sequence detection system. A control cDNA dilution series was created for each gene to establish a standard curve. Reverse transcriptase was excluded from control samples to identify potential genomic contamination. Each reaction was subjected to melting point analysis to confirm single amplified products. The data generated from each PCR were analyzed using MXP 3000 software.

Quantitative real time PCR was used to verify the microarray results for growth hormone. RNA samples from each treatment were reverse-transcribed into cDNA and amplified using real time PCR. Values for growth hormone were normalized to values obtained for the housekeeping gene, glyceraldehyde-3-phosphate dehydrogenase, and the ratios of the two treatments were calculated. In both the C2C12 and TM3 cell lines differential expression was qualitatively confirmed.

Using the $\Delta\Delta C_t$ method, relative expression was calculated. In C2C12, 20HE treatment increased growth hormone expression between 3 and 4 times greater than control. In TM3, 20HE treatment increased growth hormone expression between 6 and 8 times greater than control, as shown in Table 4. In comparison, methandrostenolone had little or no effect on growth hormone expression in either the C2C12 or TM3 cell lines.

To further investigate the effects of 20-HE, the TM3 leydig cell line was treated for varying intervals, from 20 minutes to 24 hours, with either 20-HE or methandrostenolone. Growth hormone expression was than analyzed using real time PCR as mentioned earlier. As shown in Table 5, 20-HE treatment increased growth hormone expression over time, beginning after 45 minute and remaining increased after 24 hours. Methandrostenolone treatment elicited very little change in growth hormone expression over time.

TABLE 4

Growth Hormone Expression in Two Murine Cell lines using Real Time RT-PCR

| Cell Line | Treatment | Expression Relative to Control |
|---|---|---|
| TM3 | 1 µM 20-Hydroxyecdysone | 7.1 ± 1.2 |
|  | 1 µM Methandrostenolone | 2.3 ± 1.4 |
| C2C12 | 1 µM 20-Hydroxyecdysone | 3.9 ± 0.9 |
|  | 1 µM Methandrostenolone | 0.8 ± 0.5 |

TABLE 5

Time Course of Growth Hormone Expression in TM3 cells using Real Time RT-PCR

| Incubation Time | 1 µM 20-hydroxyecdysone Growth Hormone Expression | 1 µM Methandrostenolone relative to Control |
|---|---|---|
| 20 m | 0.9 | 1.2 |
| 45 m | 3.5 | 1.9 |
| 1 hr | 7.3 | 2.5 |
| 2 hr | 6.9 | 1.7 |
| 4 hr | 7.2 | 2.1 |
| 24 hr | 7 | 2.3 |

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

TABLE 3

Primer Pairs for Murine genes analyzed

| Gene | Forward Primer | Reverse Primer |
|---|---|---|
| Growth Hormone | AAAGAGTTCGAGCGTGCCTACAT SEQ ID NO: 1 | AGAAAGCAGCCTGGGCATTC SEQ ID NO: 2 |
| Glyceraldehyde-3-phosphate Dehydrogenase | TGTGTCCGTCGTGGATCTGA SEQ ID NO: 3 | CCTGCTTCACCACCTTCTTGA SEQ ID NO: 4 |

What is claimed is:

1. A method of treatment of muscle in a mammal comprising administering a composition comprising an effective amount of an ecdysteroid, wherein the treatment is to treat muscle degradation, to treat muscle atrophy, or to treat cachexia.

2. The method of claim 1, wherein the ecdysteroid is 20-hydroxyecdysone.

3. The method of claim 1, wherein the ecdysteroid is a phytoecdysteroid.

4. The method of claim 1, wherein the composition is an extract of a plant.

5. The method of claim 1, wherein the composition is an extract of spinach.

6. The method of claim 1, wherein the composition further comprises at least one additive.

7. The method of claim 6, wherein the additive is a pharmaceutically acceptable carrier, excipient, diluent or solvent.

8. The method of claim 1, wherein the composition is formulated as a capsule, tablet, syrup, concentrate, powder, granules, aerosol, or bead.

9. The method of claim 1 wherein the composition is administered in a therapeutically effective amount of about 0.01 mg/kg per day to 5 mg/kg per day.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaagagttcg agcgtgccta cat                                              23

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agaaagcagc ctgggcattc                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgtgtccgtc gtggatctga                                                  20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctgcttcac caccttcttg a                                                21